United States Patent [19]

Ulick

[11] 4,081,538
[45] Mar. 28, 1978

[54] ALDOSTERONE ANTAGONISTS

[76] Inventor: Stanley Ulick, 38 Crane Rd., Scarsdale, N.Y. 10583

[21] Appl. No.: 746,847

[22] Filed: Dec. 2, 1976

[51] Int. Cl.$^2$ .................. A61K 31/58; C07J 17/00
[52] U.S. Cl. ...................... 424/241; 260/239.55 R
[58] Field of Search ..................................... 424/241

[56] References Cited
U.S. PATENT DOCUMENTS 2,959,586 11/1960 Kerwin et al. ............ 260/239.55
3,178,346 4/1965 Wettstein et al. .......... 260/239.55

OTHER PUBLICATIONS

Kagawa et al., Science, vol. 126 (1957) p. 1015.
Funder et al., Endocrinology, (99) p. 619 (1976).
Adam et al., Endocrinology (1978).

Primary Examiner—Elbert L. Roberts
Attorney, Agent, or Firm—Hubbell, Cohen, Stiefel & Gross

[57] ABSTRACT

A method for increasing the excretion of sodium by inhibiting the effect of mineralocorticoids, involving the administration to a patient of a therapeutically effective amount of an 11β,18-oxidopregnane as an aldosterone antagonist.

4 Claims, 1 Drawing Figure

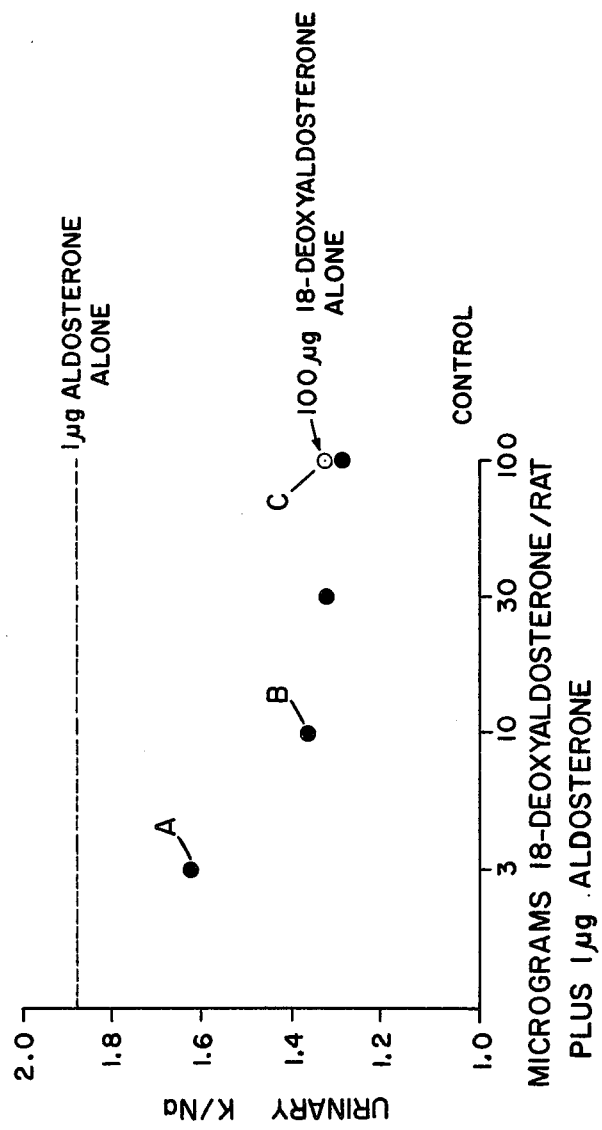

ALDOSTERONE ANTAGONISTS

BACKGROUND OF THE INVENTION

This invention relates to a method for inhibiting the effect of mineralocorticoids on urinary sodium excretion, and more particularly to the pharmaceutical administration of a class of compounds which have been found useful as aldosterone antagonists to counteract the salt-retaining effects of aldosterone and other natural mineralocorticoids.

Excessive accumulation of salt and/or fluid in the body is a common problem in medicine, occurring in a large number of disorders of diverse origin in the course of liver, kidney and heart disease. A common factor in these conditions is over-production of the adrenal salt-retaining hormone, aldosterone. This hormone normally functions to protect the body against excessive salt loss; however, the underlying disorder may stimulate its excessive secretion resulting in the accumulation of edema. Excessive secretion of aldosterone in these edema states complicates the effect of other therapeutic measures, such as the use of diuretics. Management of such disorders is greatly improved by the administration of an aldosterone antagonist to block or neutralize the over-secretion of aldosterone.

Another disorder in which sodium balance plays a major part is hypertension, where the two determinants of blood pressure, intravascular volume and vasoconstriction, are sodium-dependent. An agent which can counteract the natural salt-retaining hormone thus provides an important therapeutic modality in the treatment of hypertension.

The only aldosterone antagonist currently in clinical use belongs to the class of 17-spirolactones. These materials are described in U.S. Pat. No. 3,013,012, and are derivatives of the male hormone, testosterone, but additionally contain a 17α-propionic acid substituent which lactonizes with the 17β-hydroxyl group. The 7α-acetylthio derivative, spironolactone [3-(3-oxo-7α-acetylthio-17β-hydroxy-4-androstene-17α-yl) propionic acid lactone] has been a useful therapeutic agent, either alone or in combination with diuretic agents.

One disadvantage of the currently available aldosterone antagonist, spironolactone, is the need to administer relatively large doses, of 100 mg. or more, e.g., as much as 400 to 600 mg. per day, of the active ingredient, to obtain a therapeutically effective blood level. Such doses may be several thousand times more than the normal secretory rate of aldosterone (i.e., 100 micrograms per day). The necessity for such large dosages does not necessarily result from low affinity for the mineralocorticoid target cell since the affinity of spironolactone is approximately one-tenth that of aldosterone. Rather, the discrepancy between the in vitro and in vivo potency of spironolactone results, inter alia, from the various metabolic pathways of the spirolactone in the body which diminish its activity.

The necessity for a large dosage of a drug, such as spironolactone, for which there exists several naturally-occurring receptors and biosynthetic systems in the body, increases the likelihood of side effects based on mistaken recognition of the drug by these receptors and biosynthetic systems.

Spironolactone has been implicated in the development of steroid hormone-dependent breast cancer (Loube, et al, Breast Cancer Associated with Administration of Spironolactone, Lancet I (1975), p. 1428). While this possible side effect may lack statistical validation, long term studies in rodents have shown that spironolactone is tumorigenic and the FDA has recommended that its use be restricted to patients in whom other therapy is inadequate (FDA Drug Bulletin, p. 33, August-October 1976).

The more common side effects of spironolactone therapy, male gynecomastia and impotence, are the result of two factors, the androgen antagonist action of the spironolactone and its inhibition of testosterone biosynthesis (Siiteri et al, Mechanism of Spironolactone (Sp) Induced Gynecomastia, Fifty-Sixth Annual Meeting, The Endocrine Society, Atlanta, 1974, Abstract 187). This is not surprising since the 17-spirolactones are derivatives of the male hormone testosterone.

It is, accordingly, among the objects of the present invention to provide new aldosterone antagonists which exhibit greater mineralocorticoid receptor affinity and antagonist activity and which are more stable than the 17-spirolactones such as spironolactone, and which may thus be utilized to counteract excessive, aldosterone-stimulated salt retention with decreased risk of side reactions.

Other objects and advantages of the therapeutic method of the invention employing such materials will be apparent from the following description of preferred forms thereof.

SUMMARY OF THE INVENTION

In accordance with the present invention, a therapeutic method is provided for inhibiting the effect of mineralocorticoids on urinary sodium excretion, by administering to a patient a therapeutically effective amount of an 11β,18-oxidopregnane as an aldosterone antagonist. The 11β,18-oxidopregnanes useful in the present method may be administered in markedly lower dosages, typically at about one-tenth the dosage, of the material (spironolactone) clinically employed as an aldosterone antagonist at the present time.

The natural salt-retaining hormone aldosterone possesses the following formula:

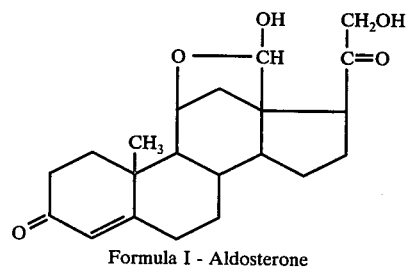

Formula I - Aldosterone

It has now been found that removal of the 18-hydroxyl group of the hemiacetal form of aldosterone results in antagonist rather than agonist activity. Thus, the prototype of the 11β,18-oxidopregnanes useful in the practice of the method hereof, 18-deoxyaldosterone (21-hydroxy-11-β,18-oxido-4-pregnene-3,20-dione), has the following formula:

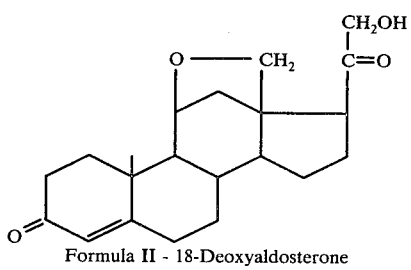

Formula II - 18-Deoxyaldosterone

This compound, and other 11β,18-oxidopregnanes, exhibit high mineralocorticoid receptor affinity and antagonist activity, increased stability, and decreased risk of side reactions compared to the 17-spirolactones, and thus provide a new type of aldosterone antagonist available for pharmaceutical use.

It is believed that the 11β,18-oxidopregnanes (including the pregnenes and pregnadienes), because of their close structural resemblance to the cyclic hemiacetal form of the natural sodium-retaining hormone (lacking only the 18-hydroxyl group thereof), interact with high affinity with the receptor sites of the natural hormone's target cells but fail to initiate a biologic effect. The high affinity of the 11β,18-oxidopregnanes to these receptors prevents access of aldosterone and in this manner neutralizes or blocks the biological effect of the natural hormone.

The basis of the antagonist action of 11β,18-oxidopregnanes on aldosterone and other mineralocorticoids is the conformational similarity between this class of compounds and the natural hormone at the C-ring and their corresponding points of attachement to the mineralocorticoid receptor protein. This conformational similarity is sufficient to strongly bind the 11β,18-oxidopregnane to the receptor protein, while failing to form an active steroid-receptor complex capable of nuclear translocation and initiation of biologic effect, and at the same time preventing access of the natural hormone to its receptor.

The 11β,18-oxidopregnanes are characterized by the presence of the 11β,18-oxido ring:

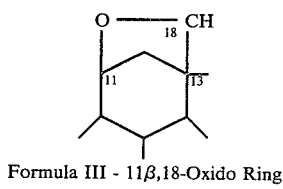

Formula III - 11β,18-Oxido Ring

Compounds incorporating this moiety are rapidly absorbed from the gastrointestinal tract without the necessity for providing therein any nuclear substituents which might be metabolically removed. Further, unlike the 17-spirolactones (which are androstanes rather than corticosteroids), the 11β,18-oxido compounds utilized herein are recognized as adrenal steroids rather than androgens and therefore do not occupy the hormonal receptors of the sex steroids and compete with their natural biosynthetic precursor substrates. Moreover, the natural occurrence of the 11β,18-oxido grouping and the similarity to the parent hormone results in both a wide margin between therapeutic and toxic effects and greater efficacy at lower dosages. The natural occurrence of the 11β,18-oxido grouping is illustrated by the following: 18-deoxyaldosterone [Formula (II)] serves as a biogenic precursor of aldosterone in microorganisms [Kondo et al, JACS, 87, 4655 (1965)], and in mammalian adrenal systems [Ulick, Excerpta Med. Int. Cong. Ser. 273, 761, 1972]. Similarly, two 11β,18-diepoxy derivatives are natural metabolites of aldosterone which have been isolated from human urine [Kelly et al, Biochemistry 1, 172 (1962)].

It should be understood that the therapeutic method of this invention is not, however, restricted to the mechanisms proposed hereinabove, but rather resides in the aldosterone antagonism of the 11β,18-oxidopregnanes employed herein, whatever their pharmacodynamic mode of operation.

The 11β,18-oxidopregnanes useful herein may comprise either the saturated or unsaturated corticosteroids. Use of the latter, unsaturated 11β,18-oxido compounds, e.g., the $\Delta^1$ or $\Delta^4$, 11β,18-oxidopregnenes or the $\Delta^1$, $\Delta^4$, 11β,18-oxidopregnadienes, is in fact preferred. Of greatest interest as aldosterone antagonists are the 3-keto-4-pregnenes or the 3-βhydroxy-5-pregnenes, which are metabolically convertible to the 3-keto-4-pregnenes in vivo.

While compounds useful as aldosterone antagonists in accordance with the present method necessarily contain the 11β,18-oxido grouping in the C-ring, it will be understood that various recognized structural modifications may be made in the pregnane nucleus thereof to enhance their absorption rate or decrease their metabolism to inactive forms provided only that such modifications do not significantly alter the favorable antagonist-/agonist ratio exhibited by the base compounds.

With the exception of halogen substitution at the tertiary carbon position at C-9, which leads to enhanced mineralocorticoid activity, the preferred positions for modification of the pregnane nucleus are the methylene groups at carbon atoms 1, 2, 6, 7, 15 and 16. Each pair of adjacent carbon atoms may be the site of a double bond or the methylene groups themselves may be substituted by hydroxyl groups, esters, or ethers, by keto groups, including their carbonyl derivatives (e.g., oximes, hemicarbazones or hydrazones); by carboxyl groups, including their esters, or the corresponding thio derivatives of any of the above. Compounds which may thus be utilized as aldosterone antagonists in accordance with this invention may have the following formula:

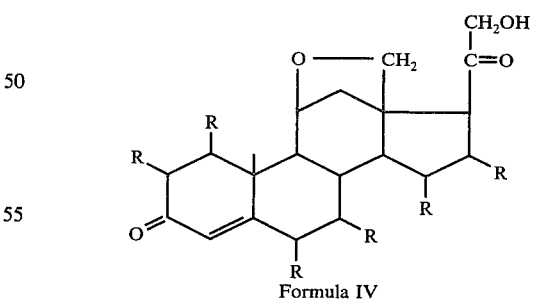

Formula IV in which the methylene groups of the pregnane nucleus at the indicated positions may be the situs of double bonds, or be substituted by the R moieties, which may be the same or different, and which may be hydroxyl groups, esters or ethers, keto groups or their carbonyl derivatives, carboxyl groups or their esters, or the corresponding thio derivatives of the preceding.

Thus, it is known that dehydrogenation, for example at the 1,2-positions, decreases the rate of reduction of corticosteroids to biologically inactive forms, as in the case of the Δ¹ derivatives of cortisone, cortisol and aldosterone. Similarly, it is known that lower alkyl (C 1-4), particularly methyl, substitution at the 6-position, as in 6α methylprednisone, or the 16-position as in dexamethasone and triamicinolone (16α) or betamethasone (16β) leads to enhanced potency relative to the natural glucocorticoid, hydrocortisone. Similarly, it is known that C-7 substitution as for example the 7α-substituted spirolactones can lead to enhanced in vivo potency.

It is also known that certain hydroxylation of the steroid nucleus, for example 1α-hydroxylation of corticosterone, leads to considerable enhancement of mineralocorticoid receptor affinity and biological activity (Idler et al, J. Fish. Res. Bd. of Canada 24:205, 1967). Additionally, it is recognized that halogen (particularly fluoro), substitution may enhance activity. In the case of 9α-fluorohydrocortisone, for example, the halogen substitution additionally imparts increased affinity for the mineralocorticoid receptor, approaching that of the natural hormone aldosterone. Accordingly, the 11β,18-oxidopregnanes useful in the method of this invention may be unsubstituted or, if desired, substituted, for example, by lower alkyl groups (e.g., methyl) at the 6, 7 or 16-positions, and by halogen (e.g., fluoro) groups at the 6 and/or 9-positions and, as indicated below, by oxo or hydroxy groups at the 20-position and by hydroxy or ester groups at the 21-position.

It will be understood that the 11β,18-oxidopregnanes useful herein may also be further substituted, as more fully described hereinafter.

The 11β,18-oxidopregnane aldosterone antagonists are readily synthesized by acid-catalyzed dehydration of the corresponding 11β,18-diols or derivatives thereof, e.g., an 18-acyl derivative. The diol precursors can themselves be prepared by reduction of the 11β-hydroxy-18-oic acid lactones or corresponding 11β-hydroxy-18-oxo derivatives. See, for example, Schmidlin et al, Helvetica Chimica Acta 44, Fasc. 6, 1596 (1961).

Alternatively, the aldosterone antagonists may be synthesized by the microbiological C-18-hydroxylation of corresponding corticosterones [Kondo et al, JACS 87, 4655 (1965)] to yield 18-hydroxycorticosterone dimers from which the 11,18-oxido derivatives are obtained by treatment with acid.

The 11β,18-oxido compounds may also be prepared from 11β-hydroxypregnanes containing an unactivated angular methyl group, as disclosed by Heusler et al, Angewandte Chemie 3, 525 (1964).

Finally when, as indicated hereinafter, 11β-18-oxidopregnanes whose C-18 and C-20 carbon atoms are bonded to one another are to be employed as aldosterone antagonists, such may be synthesized in the manner of the photolysis of the 20-keto pregnanes described in Li et al, Journal of Organic Chemistry, 41, 2552 (1976). Alternatively, related 11β,18,18,20-diepoxy pregnanes can be synthesized by the action of lead tetraacetate on the corresponding 18,20-oxidopregnanes (Beal et al, Chemistry and Industry, p. 1505 (1960); and Beal et al U.S. Pat. No. 3,216,998).

The aldosterone antagonists may be utilized, as indicated hereinabove, in dosages substantially lower than heretofore required for aldosterone antagonists of the spirolactone type. They may be administered in any suitable dosage form, e.g., formulated with any known organic or inorganic pharmaceutical carrier. Carriers so utilized should be inert (non-reactive) relative to the 11β,18-oxido compounds.

The aldosterone antagonists are preferably orally administered, for example, in tablets, capsules or the like. Conventional carriers, e.g., gelatin, lactose, starches or the like may be incorporated therein. If desired, the preparations may be sterilized or may additionally contain known auxiliary substances, such as preserving, stabilizing, wetting or emulsifying agents, salts for regulating osmotic pressure, buffers, extenders and/or other conventional carriers and the like. The content of active substances in these preparations, such as an ampoule or a tablet, may be within the range of from about 5 to 100 milligrams, preferably from about 5 to 10 milligrams.

BRIEF DESCRIPTION OF THE DRAWING

In the annexed drawing the effect of 18-deoxyaldosterone, one of the aldosterone antagonists of the present invention, on blocking of the mineralocorticoid effect of aldosterone, is graphically illustrated.

PREFERRED EMBODIMENTS OF THE INVENTION

The 11β,18-oxidopregnanes which may be employed as aldosterone antagonists in accordance with the present invention may, as indicated hereinabove, incorporate varying substituents designed to enhance absorption or delay metabolism in a manner known per se in the steroid art. As previously noted, the basic 11β,18-oxidopregnane may be thus substituted at any carbon atom of the pregnane skeleton containing a substitutable hydrogen atom, viz., any position other than C-10 and C-13, as by hydroxyl groups or their ethers or esters, or by carboxyl groups or their esters, or corresponding thio derivatives, or by halogen or lower alkyl groups. In the case of carbon atoms containing two substitutable hydrogens (any other than C-5,8,9,10,13 and 14) the pregnanes may also be substituted by oxo groups (or their carbonyl derivatives) prepared by oxidation of the corresponding secondary alcohols. Also, the pregnanes may be unsaturated, particularly at the 1, 2 and/or 4, 5-positions, or the 4, 5 double bond may be reduced especially to the 5α configuration. Saturation to the 5α configuration may actually enhance steroid target cell receptor binding and increase biological activity. Other modifications that are permissible, provided they do not impair the binding affinity of the 11β,18-oxidopregnane to mammalian mineralocorticoid receptors, involve removal of the 19-methyl group or the 21-hydroxyl group or substitution of the latter by an ester moiety. Finally, one of the C-18 hydrogens may be substituted by a second oxide ring bridging C-18 and C-20, or the C-18 and C-20 carbon atoms may be directly bonded to one another to form an 18,20-cyclo derivative.

It should further be apparent from the preceding that 11β,18-oxidopregnanes of the preceding types which are useful as aldosterone antagonists in the practice of the method of this invention include both racemic and optically active forms of any desired configuration.

A preferred class of the 11β,18-oxidopregnanes useful herein comprises those compounds of the formula:

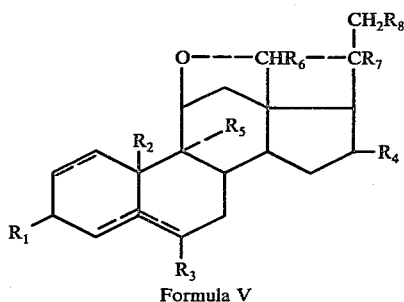

Formula V

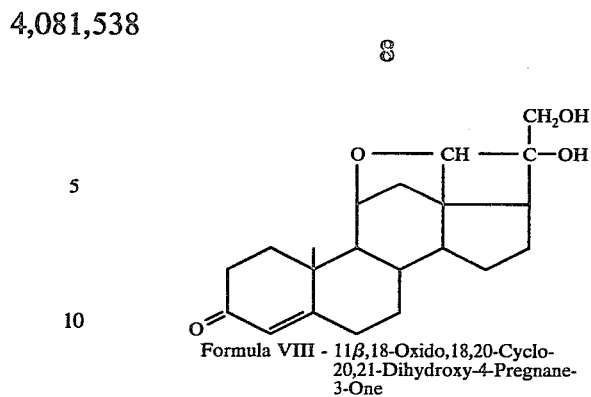

Formula VIII - 11β,18-Oxido,18,20-Cyclo-20,21-Dihydroxy-4-Pregnane-3-One wherein:

R₁ is oxo or hydroxy,

R₂, R₃ and R₄ are each hydrogen or lower alkyl ($C_{1-4}$), preferably methyl,

R₅ is hydrogen or halo (preferably fluoro),

R₆ is hydrogen, or a covalent bond or ether linkage bonding the $C_{18}$ and $C_{20}$ carbons to one another, R₇ is oxo or hydroxy, and R₈ is hydrogen, hydroxy or an ether or ester group OR₉ wherein R₉ is lower alkyl ($C_{1-4}$) or acyl.

Particularly preferred among the 11β,18-oxidopregnanes thus useful are the 4-pregnene-3,20-diones having the formula:

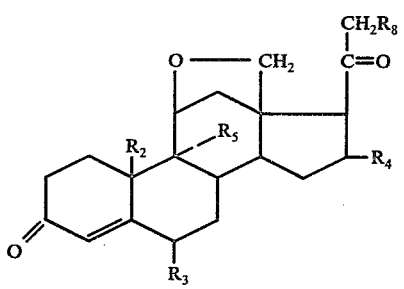

wherein R₂, R₃, R₄, R₅ and R₈ are as defined above.

When 11β,18-oxidopregnanes of the preceding types (V or VI) are employed, and the C-21 carbon is esterified, the acyl group R₉ may, if desired, comprise any suitable acyl radical of an organic acid such as those described in column 2, line 34 to column 3, line 5 of Wettstein et al U.S. Pat. No. 3,178,346, organic carboxylic acids, particularly those containing from 1 to 12 carbon atoms, being preferred.

Those 11β,18-oxidopregnanes whose use is particularly preferred in the method of the present invention include 18-deoxyaldosterone (Formula II above), as well as the following further compounds:

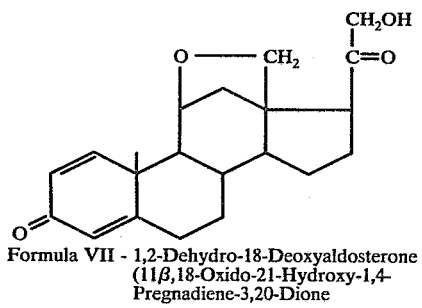

Formula VII - 1,2-Dehydro-18-Deoxyaldosterone
(11β,18-Oxido-21-Hydroxy-1,4-Pregnadiene-3,20-Dione)

The use of 18-deoxyaldosterone (Formual II) as a mineralocorticoid, but not its use as an aldosterone antagonist, has been suggested in Wettstein et al U.S. Pat. No. 3,178,346. Similarly, possible antihormonal activity, but not aldosterone antagonism, has been suggested as one of a wide variety of possible activities of related diepoxy 11β,18-oxidopregnanes in the aforesaid Beal et al U.S. Pat. No. 3,216,998.

In regard to 1,2-dehydro-18-deoxyaldosterone (Formula VII) such compound has been found to exhibit substantially the same potency as 18-deoxyaldosterone in vitro. This compound may, however, possess greater activity than 18-deoxyaldosterone in vivo, 1,2-dehydrogenation being known to decrease the rate of reductive metabolism in corticosteroids.

SPECIFIC EXAMPLES OF THE INVENTION

The following examples illustrate preferred techniques for the preparation of 11β,18-oxidopregnanes useful herein, and document the aldosterone antagonist activity of two preferred members, i.e., 18-deoxyaldosterone and 1,2-dehydro-18-deoxyaldosterone, of that class. In the examples all parts and percentages are given by weight, unless otherwise indicated.

SYNTHESIS OF THE 11β-18-OXIDO PREGNENES

EXAMPLE 1 — Preparation of 18-Deoxyaldosterone 18-deoxyaldosterone was prepared by acid-catalyzed dehydration of 18-hydroxycorticosterone, the latter having been, in turn, prepared biosynthetically employing slices of aldosterone-producing adrenal tissue [Ulick et al, Methods in Enzymology, 36, p. 503 (1975)]. The 11,18-diol (1.0 mg.) in 10 ml 1,2-dichloroethane saturated with p-toluenesulfonic acid was heated under reflux for 30 minutes. The solvent was washed with dilute sodium carbonate and water, dried and evaporated. Chromatographic analysis of the residue revealed 18-deoxyaldosterone as the major product of 18-hydroxycorticosterone along with small amounts of starting material and its etiolactone derivative. 18-deoxyaldosterone migrated at 1.06 (±0.02) the rate of 11-dehydrocorticosterone in the toluene/formamide or methylcyclohexane:toluene (1:1)/formamde paper chromatographic systems. Its properties agreed with those of reference samples prepared by a published method [Kondo et al, JACS 87, 4655 (1965)]. Its 21-acetylated derivative prepared in the usual way with acetic anhydride:pyridine migrated at a slightly faster rate (1.05 ±0.02) than 21-acetoxy-11-dehydrocorticosterone in methylcyclohexane:toluene (1:1)/formamide.

EXAMPLE 2 — Preparation of 1,2-Dehydro-18-Deoxyaldosterone

Commercially available 1,4-pregnendiene-3-one was incubated with aldosterone-producing adrenal tissue and $\Delta^1$ 18-hydroxycorticosterone isolated chromatographically. The diol was then converted to the 11β,18-oxido derivative by refluxing for 30 minutes in ethylene dichloride containing p-toluenesulfonic acid in the same manner described in connection with Example 1 above.

ALDOSTERONE ANTAGONIST ACTIVITY

EXAMPLES 3 and 4

Competitive Binding of 11β,18-Oxidopregnanes to the Mineralocorticoid Receptor in Vitro The ability of the aldosterone antagonists of the invention to compete with the natural hormone at its active site was determined in vitro, using a preparation of mammalian mineralocorticoid receptor. In particular, binding of 18-deoxyaldosterone and $\Delta^1$-18-deoxyaldosterone was compared with aldosterone and spirolactone and its two major metabolites, as follows:

Kidney slices from adrenalectomized male Sprague-Dawley rats were incubated with $2 \times 10^{-9}$ M $^3$H-aldosterone and relative binding of the respective steroids was determined in the manner described by Funder et al, Biochemical Pharmacology, 23, 1493 (1974). The comparative data thus obtained is set forth in Table I below, the results therein being expressed in terms of the amount of steroid required to displace 50% of the labeled aldosterone tracer. The results tabulated for the three 17-spirolactones are taken from Funder et al.

TABLE I

Competition of Antagonists with Aldosterone for Mammalian Mineralocorticoid Binding Sites

| Example or Control | Steroid | Steroid required for 50% reduction of $^3$H-aldosterone binding | Relative dose antagonist: aldosterone |
|---|---|---|---|
| — | Aldosterone | mols<br>$5.6 \times 10^{-9}$ | |
| Ex. 3 | 18-Deoxyaldosterone | $2.0 \times 10^{-8}$ | 3.6 |
| Ex. 4 | $\Delta^1$-18-Deoxyaldosterone | $3.0 \times 10^{-8}$ | 5.3 |
| Control A | SC 9420 | $3.5 \times 10^{-8}$ | 6.3 |
| Control B | SC 9376 | $1.2 \times 10^{-7}$ | 21.5 |
| Control C | SC 14266 | $1.3 \times 10^{-6}$ | 230 |

SC 9420 = spironolactone.
SC 9376 = aldadiene, 3-(3-oxo-17β-hydroxy-4,6-androstadien-17α-yl) propionic acid α-lactone.
SC 14266 is the corresponding open ring hydroxy acid of aldadiene.

From the tabulated data it will be seen that 18-deoxyaldosterone exhibited the greatest affinity, next to aldosterone itself. The two major metabolites of spironolactone (to which spironolactone is converted in the body) exhibited lesser affinity.

EXAMPLE 5 — Competitive Binding of 11β,18-Oxidopregnanes to the Mineralocorticoid Receptor Following In Vivo Administration A measure of the affinity of 18-deoxyaldosterone for the mineralocorticoid receptor in vivo was determined following intravenous administration, along with labeled aldosterone tracer, to adrenalectomized male Sprague-Dawley rats. The rats' kidneys were removed, and the dose required to reduce binding of the tracer hormone by 50% was determined employing the method of Funder et al, Endocrinology, 92, 994 (1973). The comparative binding of aldosterone and SC 26304, a 17-spirolactone having an in vitro affinity for the receptor even greater than that of aldosterone itself (Funder et al, Endocrinology, supra), is set forth in the following tabulation:

TABLE II

Competition of Antagonists Compared to Aldosterone for Mammalian Mineralocorticoid Receptor Following Intravenous Injection in Adrenalectomized Rats

| Example or Control | Steroid | Dose required for 50% reduction of $^3$H-aldosterone binding | Antagonist: aldosterone ratio |
|---|---|---|---|
| | | μg | |
| | Aldosterone | 0.3 | |
| Ex. 5 | 18-Deoxyaldosterone | 3.0 | 10:1 |
| Control D | SC 26304 | 60 | 200:1 |

SC 26304 is the 7 α-carboxyisopropyl ester analog of spironolactone.

As indicated in the preceding table, under the indicated circumstances the antagonist:agonist ratio for 18-deoxyaldosterone was 10:1 whereas 200 times that amount of spirolactone was required to obtain a comparable effect. This illustrate one disadvantage implicit in the use of the spirolactones as antagonists, the marked disparity between their in vitro and in vivo effectiveness because of rapid metabolism to less active forms.

EXAMPLE 6 — Bioassay of Antagonist Activity

The ability of the 11β,18-oxidopregnanes of the present invention to antagonize the effect of the natural sodium-retaining hormone was demonstrated by administering such substances to adrenalectomized rats and observing a reversal of the aldosterone-induced reduction in urinary potassium/sodium ratio. Using the standard adrenalectomized rat bioassay for mineralocorticoid and antimineralocorticoid effects as described, for example, by Fuller et al, Journal of Steroid Biochemistry, 7, 387 (1976), 1 μg of aldosterone administered subcutaneously to a 120-180 g Sprague-Dawley rat produces a maximal response as measured by the increase in urinary K/Na ratio.

As shown in the annexed drawing, under the same conditions the lowest dose (A) of 18-deoxyaldosterone assayed, 3 μg, significantly blocked 30% of the biological effect of 1 μg aldosterone. In the same assay a 10 μg dose (B) of 18-deoxyaldosterone blocked 59% of the sodium-retaining potassium excreting effect of 1 μg aldosterone. The largest dose (C) of 18-deoxyaldosterone, 100 μg, had a maximal blockade effect and when administered alone to the test animal, produced no significant difference in urinary K/Na ratio and thus demonstrated pure antagonist activity.

A comparison of the efficacy of 18-deoxyaldosterone and various of the 17-spirolactones as antagonists in the adrenalectomized rat bioassay is further summarized in the following tabulation, in which 18-deoxyaldosterone is shown to be more than 200 times more effective than the spirolactone (SC 9420) currently in clinical use:

TABLE III

Minimally Effective Dose Ratio of Antagonist Required to Significantly Block the Effect of Aldosterone on Urinary Sodium/Potassium Ratio in Adrenalectomized Rats

| Example of Control | Antagonist | Antagonist/aldosterone ratio |
|---|---|---|
| Ex. 6 | 18-Deoxyaldosterone | 3 |
| Control E | SC-14266[1] | 3000 |
| Control F | SC-9420[2] | 650 |

TABLE III-continued

Minimally Effective Dose Ratio of Antagonist Required to Significantly Block the Effect of Aldosterone on Urinary Sodium/Potassium Ratio in Adrenalectomized Rats

| Example of Control | Antagonist | Antagonist/aldosterone ratio |
|---|---|---|
| Control G | SC-26304[2] | 600 |

[1]Data from Kagawa et al, Arch. Int. Pharmacodyn. 149, 8 (1964).
[2]Data from Cella, Edema: Mechanisms and Management. A Hahnemann Symposium on Salt and Water Retention (Moyer J. H. and Fuchs, M., eds.). Philadelphia, W. B. Saunders, 1960, p. 303. Data based on the assumption that aldosterone is 25 times more potent than 11-deoxycorticosterone acetate.
[3]Data from Marver et al, Proceedings, National Academy of Sciences USA 71, 1431 (1974).

EXAMPLE 7 — Comparison of 11β,18-Oxidopregnanes and 17-Spirolactones as Aldosterone Antagonists As indicated hereinabove, one disadvantage of the currently available aldosterone antagonist, spironolactone, comprises various side effects, e.g., the androgen antagonist side effect resulting from its affinity for mammalian androgen receptors. The relative affinities for both mineralocorticoid and androgen receptors of 18-deoxyaldosterone and spironolactone are compared in the following tabulation:

TABLE IV

Comparison of Binding Affinities of Aldosterone Antagonists for Mineralocorticoid and Androgen Receptors

| Example or Control | Steroid | Dose of steroid required for 50% reduction in binding of natural hormone to its specific receptor | |
|---|---|---|---|
| | | Mineralocorticoid Steroid/aldosterone | Androgen Steroid/dihydrotestosterone |
| Example 7 | 18-Deoxyaldosterone | 3.6 | 1000:1 |
| Control H | Spironolactone | 6.3 | 50:1 |

From Table IV it will be seen that, whereas spironolactone is almost as effective as 18-deoxyaldosterone in binding to mineralocorticoid receptors, it shows much greater binding to androgen receptors where it acts as an antagonist. In contrast, 18-deoxyaldosterone demonstrated very little competition with dihydrotestosterone for the androgen receptor; therefore, 18-deoxyaldosterone would not be expected to interfere with male hormonal function when administered in therapeutically effective dosages as an aldosterone antagonist.

It will be understood that various changes may be made in the preferred embodiments of the compositions and techniques described hereinabove without departing from the scope of the present invention. The preceding description is therefore intended as illustrative only and should not be construed in a limiting sense.

What is claimed is:

1. A method for inhibiting the effect of mineralocorticoids on sodium excretion which comprises administering to a patient as 11β,18-oxidopregnane having the formula:

wherein:
$R_2$, $R_3$ and $R_4$ are each hydrogen or lower alkyl,
$R_5$ is hydrogen or halo, and
$R_8$ is hydrogen, hydroxy or an ether or ester group $OR_9$ wherein $R_9$ is lower alkyl or acyl;
in an amount sufficient to counteract the salt-retaining effects of aldosterone.

2. The method of claim 1, wherein the 11β,18-oxidopregnane is 18-deoxyaldosterone or 1,2-dehydro-18-deoxyaldosterone.

3. The method of claim 1, wherein the aldosterone antagonist is 18-deoxyaldosterone.

4. The method of claim 1, wherein the aldosterone antagonist is 1,2-dehydro-18-deoxyaldosterone.